United States Patent
Kokate et al.

(10) Patent No.: US 6,694,181 B2
(45) Date of Patent: Feb. 17, 2004

(54) METHODS AND DEVICES FOR DETECTING VULNERABLE PLAQUE

(75) Inventors: Jaydeep Y. Kokate, Maple Grove, MN (US); Eric M. DoBrava, Crystal, MN (US); Michael J. Urick, Quebec (CA)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/781,741

(22) Filed: Feb. 12, 2001

(65) Prior Publication Data

US 2002/0111558 A1 Aug. 15, 2002

(51) Int. Cl.$^7$ .............................. A61B 5/05; A61B 5/00
(52) U.S. Cl. ....................... 600/547; 600/585; 600/549
(58) Field of Search ................................ 600/546, 547, 600/549, 434, 435, 585; 606/31; 374/100, 141, 137, 179–181, 182

(56) References Cited

U.S. PATENT DOCUMENTS

| | | | |
|---|---|---|---|
| 3,273,395 A | 9/1966 | Schwarz | |
| 3,866,599 A | 2/1975 | Johnson | |
| 3,913,568 A | 10/1975 | Carpenter | |
| 3,935,744 A | * 2/1976 | Beckman | 600/549 |
| 4,005,605 A | 2/1977 | Michael | |
| RE32,204 E | 7/1986 | Halvorsen | |
| 4,602,642 A | 7/1986 | O'Hara et al. | |
| 4,699,147 A | 10/1987 | Chilson et al. | |
| 4,752,141 A | 6/1988 | Sun et al. | |
| 4,776,334 A | 10/1988 | Prionas | |
| 4,777,955 A | 10/1988 | Brayton et al. | |
| 4,784,149 A | 11/1988 | Berman et al. | |
| 4,790,324 A | 12/1988 | O'Hara et al. | |
| 4,794,931 A | 1/1989 | Yock | |
| 4,797,840 A | 1/1989 | Fraden | |
| 4,841,981 A | 6/1989 | Tanabe et al. | |
| 4,862,887 A | 9/1989 | Weber et al. | |
| 4,986,671 A | 1/1991 | Sun et al. | |
| 4,995,398 A | 2/1991 | Turnidge | |
| 5,000,185 A | 3/1991 | Yock | |
| 5,046,501 A | 9/1991 | Crilly | |
| 5,057,105 A | 10/1991 | Malone et al. | |
| 5,109,859 A | 5/1992 | Jenkins | |
| 5,161,893 A | * 11/1992 | Shigezawa et al. | 374/181 |
| 5,174,299 A | 12/1992 | Nelson | |
| 5,217,456 A | 6/1993 | Narciso, Jr. | |
| 5,237,996 A | 8/1993 | Waldman et al. | |
| 5,275,594 A | 1/1994 | Baker et al. | |
| 5,279,565 A | 1/1994 | Klein et al. | |
| 5,304,173 A | 4/1994 | Kittrell et al. | |

(List continued on next page.)

FOREIGN PATENT DOCUMENTS

WO     WO 97/10748     3/1997

OTHER PUBLICATIONS

Buja et al., "Role of Inflammation in Coronary Plaque Disruption," *Circulation*, vol. 89, No. 1, Jan. 1994, pp. 503–505.

Casscells et al., "Thermal Detection of Cellular Infiltrates in Living Atherosclerotic Plaques: Possible Implications for Plaque Rupture and Thrombosis," *The Lancet*, vol. 347, May 25, 1995, pp. 1447–1449.

(List continued on next page.)

*Primary Examiner*—Charles Marmor
(74) *Attorney, Agent, or Firm*—Fish & Richardson, P.C., P.A.

(57) ABSTRACT

Devices and methods for detecting vulnerable plaque within a blood vessel are disclosed. A system in accordance with the present invention includes a first wire having a distal end coupled to a voltage source and a proximal end coupled to an instrument capable of measuring voltage. A distal end of a second wire is also coupled to the voltage source and a proximal end of the second wire is coupled to the instrument. The amplitude of the electromotive force produced by the voltage source preferably varies with the temperature of a tissue proximate the voltage source.

6 Claims, 6 Drawing Sheets

U.S. PATENT DOCUMENTS

| | | |
|---|---|---|
| 5,313,949 A | 5/1994 | Yock |
| 5,336,178 A | 8/1994 | Kaplan et al. |
| 5,373,849 A | 12/1994 | Maroney et al. |
| 5,445,157 A | 8/1995 | Adachi et al. |
| 5,542,915 A | 8/1996 | Edwards et al. |
| 5,547,472 A | 8/1996 | Onishi et al. |
| 5,558,093 A | 9/1996 | Pomeranz |
| 5,606,974 A | 3/1997 | Castellano et al. |
| 5,617,870 A | 4/1997 | Hastings et al. |
| 5,623,940 A | 4/1997 | Daikuzono |
| 5,682,899 A | 11/1997 | Nashef et al. |
| 5,733,739 A | 3/1998 | Zakim et al. |
| 5,849,028 A | 12/1998 | Chen |
| 5,871,449 A | 2/1999 | Brown |
| 5,924,997 A | 7/1999 | Campbell |
| 5,935,075 A | 8/1999 | Casscells et al. |
| 5,957,961 A | 9/1999 | Maguire et al. |
| 6,162,184 A | 12/2000 | Swanson et al. |
| 6,197,021 B1 | 3/2001 | Panescu et al. |
| 6,293,700 B1 * | 9/2001 | Lund et al. .................. 374/181 |

OTHER PUBLICATIONS

Davies, M.J., "Detecting Vulnerable Coronary Plaques," *The Lancet*, vol. 347, May, 25, 1996, pp. 1422–1423.

Falk et al., "Coronary Plaque Disruption," *Circulation*, vol. 92, No.3, Aug. 1, 1995, pp. 657–671.

Muller e tal., "Triggers, Acute Risk Factors and Vulnerable Plaques: The Lexicon of a New Frontier," *JACC*, vol., 23, No. 3, Mar. 1, 1994, pp 809–813.

van der Wal et al., Site of Intimal Rupture or Erosion of Thrombosed Coronary Atherosclerotic Plaques is Characterized by an Inflammatory Process Irrespective of the Dominate Plaque Morphology, *Circulation*, vol. 89, No. 1, Jan. 1994, pp. 36–44.

* cited by examiner

METHODS AND DEVICES FOR DETECTING VULNERABLE PLAQUE

FIELD OF THE INVENTION

The present invention relates generally to medical devices for detecting cardiac disease. More particularly, the present invention relates to medical devices for detecting vulnerable plaque within a blood vessel.

BACKGROUND OF THE INVENTION

Therapy modalities for heart disease have traditionally focused on treating blood vessels which have become occluded (blocked) or stenotic (narrowed) by calcified plaque deposits. Blood vessels which have become occluded or stenotic in this manner may interrupt the flow of blood which supplies oxygen to the heart muscle. Occluded or stenotic blood vessels may be treated with a number of medical procedures including angioplasty and atherectomy. Angioplasty techniques such as percutaneous transluminal angioplasty (PTA) and percutaneous transluminal coronary angioplasty (PTCA) are relatively non-invasive methods of treating restrictions in blood vessels. In these procedures, a balloon catheter is advanced over a guidewire until the balloon is positioned proximate a restriction in a diseased vessel. The balloon is then inflated and the restriction in the vessel is opened. During an atherectomy procedure, the stenotic lesion is mechanically cut or abraded away from the blood vessel wall using an atherectomy catheter.

Calcified plaque deposit typically comprise hard materials. Plaque may also comprise soft materials or combinations of soft and hard materials. Soft plaque typically comprises deposits of cholesterol and other fats which build up within the blood vessels as a patient ages. The build up of plaque in the blood vessels is sometimes referred to as atherosclerosis, or hardening of the arteries.

Atherosclerosis often begins as a small injury to an artery wall. This injury triggers a cyclic cascade of injury and response, inflammation, and healing, which may ultimately lead to the narrowing of the artery. As the atherosclerotic plaque worsens, inflammatory cells, especially macrophages, collect at the site to isolate the debris of the damaged tissue. The result is a core of lipid, macrophages or foam cells and nectrotic tissue, covered by a fibrous cap of scar tissue. If the fibrous cap becomes weakened or is subjected to excessive stress, it may rupture, exposing the trombogenic contents of the core to the blood stream. If the resulting blood clot is severe enough, it may occlude the artery. If this obstruction persists in a coronary artery, a myocardial infarction may result.

Plaque deposits which are at risk of rupturing are sometimes referred to as vulnerable plaque. Vulnerable plaque typically comprises a core of soft materials covered with a fibrous cap. Many vulnerable plaque deposits do not limit the flow of blood through the blood vessels. It has recently been appreciated that vulnerable plaques which do not limit flow may be particularly dangerous because they produce no warning symptoms, but can rupture suddenly causing heart attack and death. This may occur, for example, when the vulnerable plaque ruptures, a blood clot may be formed inside the blood vessel lumen causing a blockage.

Recently, the pivotal role of inflammation in the progression of atherosclerosis has been recognized. A systemic increase in temperature is often associated with infection (e.g., a fever). Likewise, a local infection or localized damage to tissue may result in a localized increase in temperature. An increase in temperature is thought to be caused by the response of the immune system to infection, known as inflammation. It has been observed that the inflamed necrotic core of a vulnerable plaque maintains itself at a temperature which may be one or more degrees Celsius higher than that of the surrounding tissue. For example, an inflamed plaque in a human heart, where the normal temperature is about 37° C. may be at a temperature as high as 40° C.

SUMMARY OF THE INVENTION

The present invention relates generally to medical devices for detecting cardiac disease. More particularly, the present invention relates to medical devices for detecting vulnerable plaque within a blood vessel. A system in accordance with the present invention includes a first wire having a distal end coupled to a voltage source and a proximal end coupled to an instrument capable of measuring voltage. A distal end of a second wire is also coupled to the voltage source and a proximal end of the second wire is coupled to the instrument. The amplitude of the electromotive force produced by the voltage source preferably varies with the temperature of a tissue proximate the voltage source.

One embodiment of system in accordance with the present invention includes a guidewire including the first wire and the second wire. In this embodiment, a distal end of the first wire and a distal end of the second wire are coupled to form a junction. In a preferred embodiment, the first wire comprises a first material and the second wire comprises a second material which is different than the first material. Also in a preferred embodiment, the first material and the second material are selected so that an electromotive force is produced across the junction therebetween. In a particularly preferred embodiment, the first material and the second material are selected so that the amplitude of the electromotive force across the junction varies with changes in the temperature of the junction. Also in a particularly preferred embodiment the amplitude of the electromotive force produced by the junction varies with the temperature of a tissue proximate the voltage source (i.e., the temperature of the junction is effected by the temperature of tissue proximate the junction).

An additional embodiment of system in accordance with the present invention includes a catheter including a first wire having a distal end coupled to a detector and a proximal end coupled to an instrument. The catheter also includes a second wire having a distal end coupled to the detector and a proximal end coupled to the instrument. In a preferred embodiment, the detector produces a voltage which varies with the temperature of tissue located proximate a balloon of the catheter. The detector may comprise, for example, a photodiode. In this embodiment, the catheter also includes an optical fiber having a proximal end that is coupled to a light source. Light from the light source passes through optical fiber, and is collimated by a lens. This light is partially reflected by a partially reflecting surface of a reflector so that it illuminates a portion of a layer of the balloon. The layer of the balloon preferably has temperature dependent optical properties which may effect, for example, the wavelength and/or intensity of the light which is reflected by layer. The portion of the light which is reflected by this layer forms a light signal. At least a portion of this light signal passes through the partially reflecting surface of the reflector and illuminates the detector.

DETAILED DESCRIPTION OF THE INVENTION

The following detailed description should be read with reference to the drawings, in which like elements in different drawings are numbered in like fashion. The drawings which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives which may be utilized.

Figure 1:
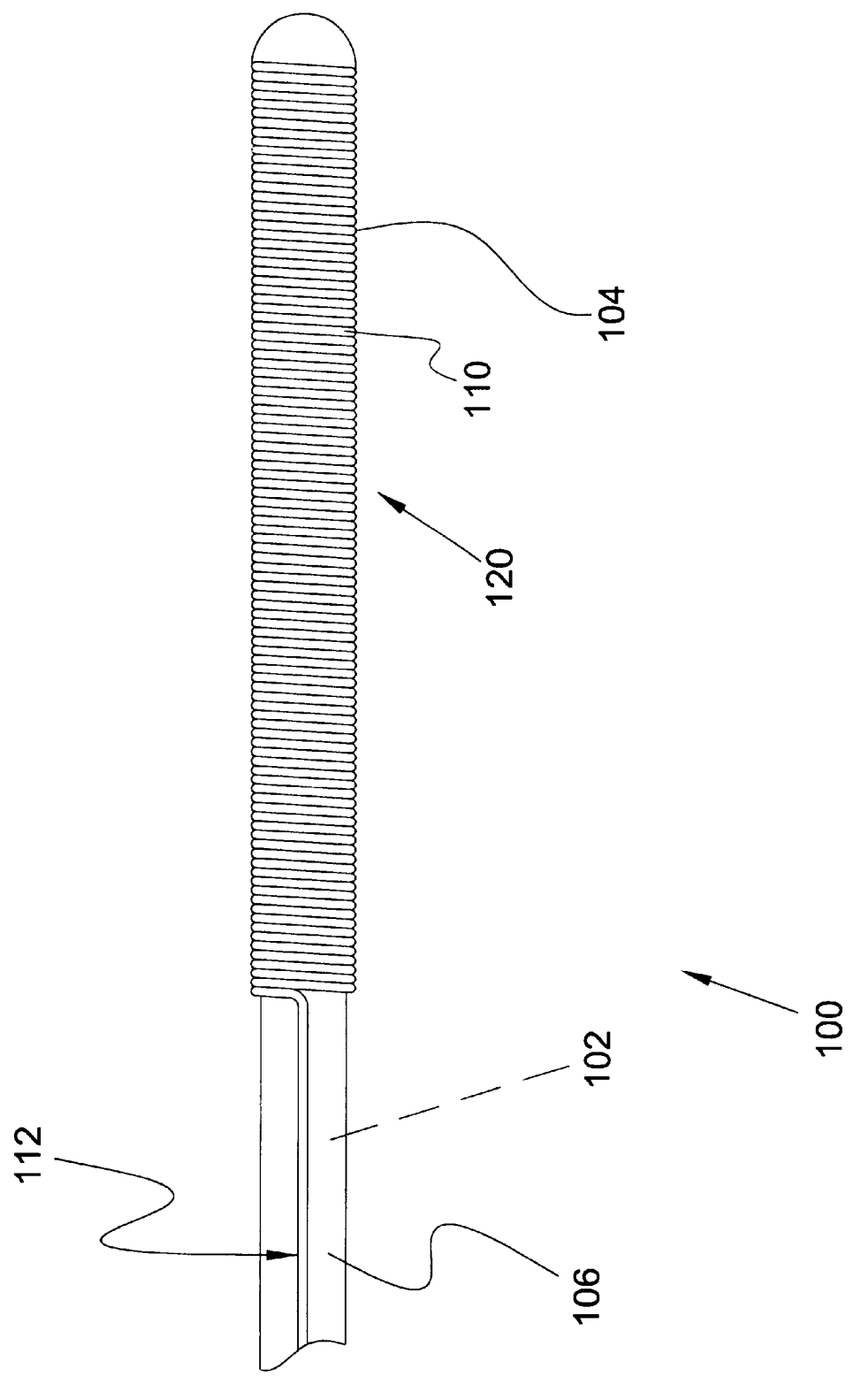
FIG. 1 is a plan view of a guidewire in accordance with an exemplary embodiment of the present invention.

FIG. 1 is a plan view of a guidewire 100 in accordance with the present invention. Guidewire 100 comprises a first wire 102, a sheath 106 disposed about first wire 102, and a coil 120 comprising a plurality of turns 110 formed by a second wire 104. In FIG. 1 it may be appreciated that second wire 104 also includes a substantially straight portion 112.

Figure 2:
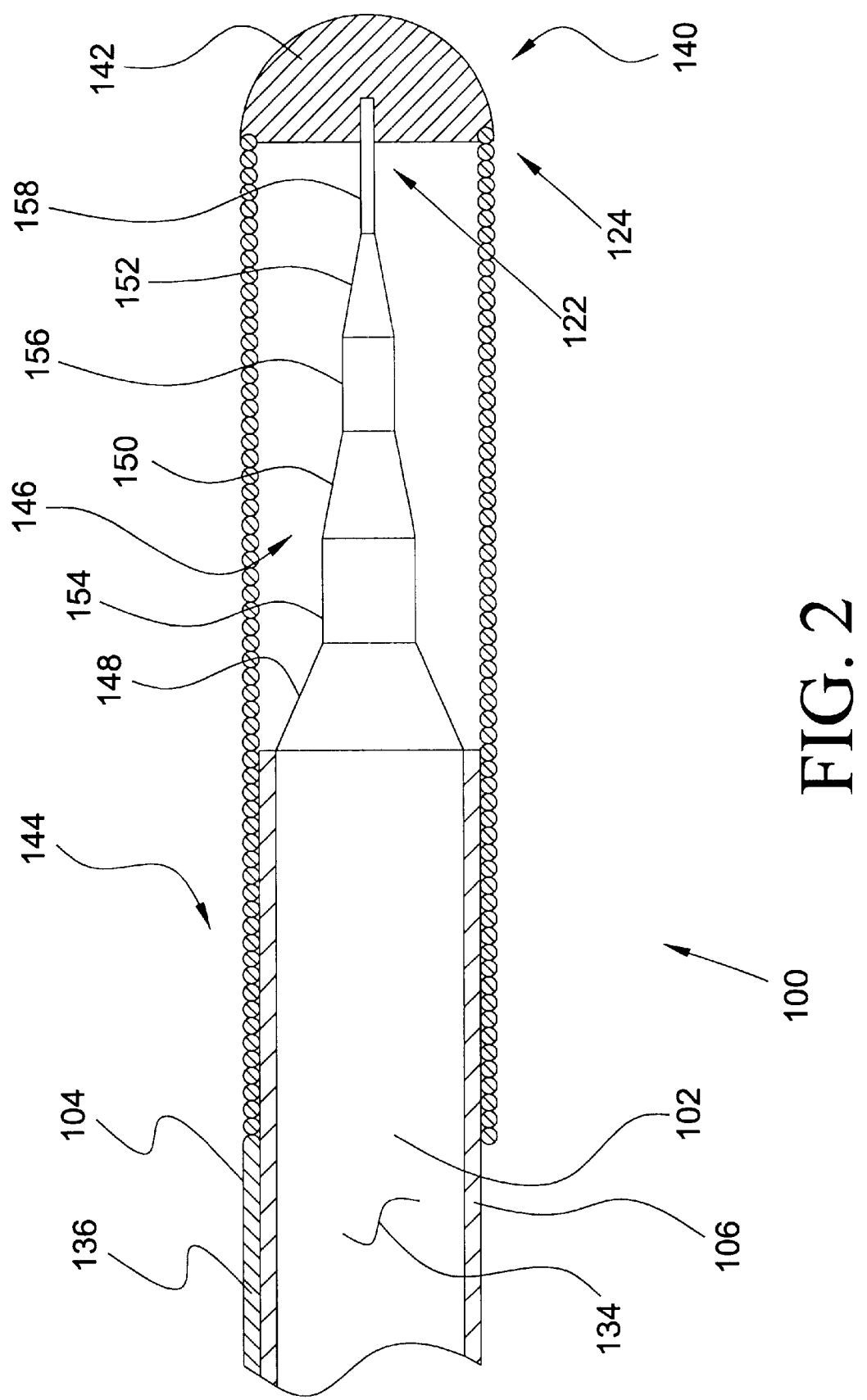
FIG. 2 is a partial cross-sectional view of a distal portion of the guidewire of FIG. 1.

FIG. 2 is a partial cross-sectional view of a distal portion of guidewire 100 of FIG. 1. In FIG. 2, it may be appreciated that a distal end 122 of first wire 102 and a distal end 124 of second wire 104 are coupled to form a junction 140. In the embodiment of FIG. 2, junction 140 includes a tip member 142 disposed between distal end 122 of first wire 102 and distal end 124 of second wire 104. In a preferred embodiment, tip member 142 comprises an electrically conductive material. Tip member 142 may be formed, for example, by depositing solder on the distal ends of first wire 102 and second wire 104.

In a preferred embodiment, first wire 102 comprises a first material 134 and second wire 104 comprises a second material 136 which is different than first material 134. In this preferred embodiment, first material 134 and second material 136 are selected so that an electromotive force is produced across junction 140. In a particularly preferred embodiment, first material 134 and second material 136 are selected so that the amplitude of the electromotive force across junction 140 varies with changes in the temperature of junction 140. For example, the relationship between the temperature of junction 140 and the electromotive force across junction 140 may be described by the relationship below for some material selections:

$$E = C_1 \times T + C_2 \times T^2 + C_3 \times T^3 + C_4 \times T^4 + C_5 \times T^5 + C_6 \times T^6 + C_7 \times T^7 + C_8 \times T^8$$

In the equation above, T represents the temperature of junction 140, E represents the electromotive force across junction 140, and C1 through C8 are constants. The values of the constants will vary depending upon which materials are selected as first material 134 and second material 136. For example, one wire may comprise chromel and the other wire may comprise constantan. By way of a second example, one wire may comprise alumel and the other wire may comprise chromel. In a particularly preferred embodiment, the amplitude of the electromotive force produced by junction 140 varies with the temperature of a tissue proximate junction 140 (i.e., the temperature of junction 140 is effected by the temperature of tissue proximate junction 140).

In the embodiment of FIG. 2, first wire 102 includes a body portion 144 and a profiled portion 146. Profiled portion 146 of first wire 102 extends between body portion 144 and distal end 122 of first wire 102. Beginning at body portion 144 and moving towards distal end 122 profiled portion 146 includes a first taper 148, a first reduced diameter portion 154, a second taper 150, a second reduced diameter portion 156, a third taper 152, and a third reduced diameter portion 158. In FIG. 2, profiled portion 146 of first wire 102 is shown in a somewhat foreshortened form for purposes of illustration. It is to be appreciated that FIG. 2 is not necessarily to scale and is somewhat diagrammatic in nature. Various embodiments of first wire 102 are possible without deviating from the spirit and scope of the present invention.

In FIG. 2, it may be appreciated that sheath 106 is disposed between first wire 102 and second wire 104. In a preferred embodiment, sheath 106 comprises a nonconductive material. Various non-conductive materials may be utilized without deviating from the spirit and scope of the present invention. Examples of materials which may be suitable in some applications include thermoplastic and non-thermoplastic materials. Examples of thermoplastic materials which may be suitable in some applications includes polyethylene (PE), polypropylene (PP), polyvinylchloride (PVC), thermoplastic polyurethane, polytetrafluoroethylene (PTFE), polyether block amide (PEBA), polyamide, and polyimide. Examples of non-thermoplastic materials which may be suitable in some applications include thermoset polyurthethane.

Figure 3:
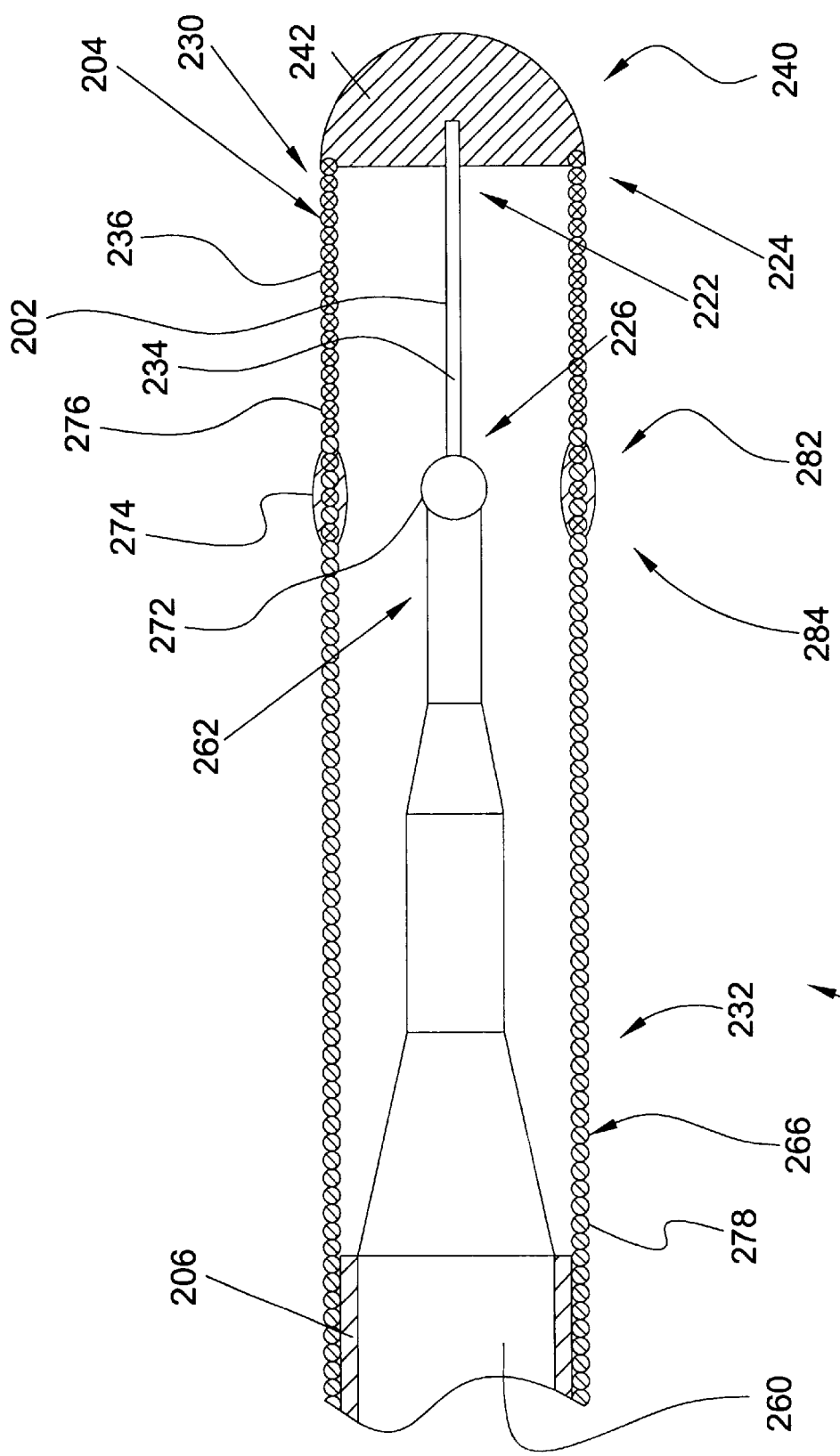
FIG. 3 is a partial cross-sectional view of a distal portion of a guidewire in accordance with an additional exemplary embodiment of the present invention.

FIG. 3 is a partial cross-sectional view of a distal portion of an additional embodiment of a guidewire 200 in accordance with the present invention. Guidewire 200 comprises a first wire 202 having a distal end 222 and a proximal end 226. The proximal end 226 of first wire 202 is fixed to a distal end 262 of a third wire 260. In the embodiment of FIG. 3, first wire 202 and third wire 260 are fixed together by a first joint 272. First joint 272 may comprise, for example, a solder joint, weld joint, and/or adhesive joint.

Guidewire 200 also comprises a second wire 204 and a fourth wire 266. Second wire 204 forms a distal coil 230 having a plurality of turns 276. In a similar fashion, fourth wire 266 forms a proximal coil 232 having a plurality of turns 278. In the embodiment of FIG. 3, a plurality of turns 276 proximate a proximal end 282 of distal coil 230 are spaced apart to accommodate a plurality of turns 278 of proximal coil 232. In a similar fashion, a plurality of turns 278 proximate a distal end 284 of proximal coil 232 are spaced apart to accommodate a plurality of turns 276 of distal coil 230. In the embodiment of FIG. 3, the distal portion of proximal coil 232 has been turned into the proximal portion of distal coil 230 so that a plurality of turns 278 of proximal coil 232 are adjacent to a plurality of turns 276 of distal coil 230. A second joint 274 connects second wire 204 of distal coil 230 to fourth wire 266 of proximal coil 232 over a plurality of turns. Second joint 274 may comprise, for example, a solder joint, a weld joint, and/or an adhesive joint.

A sheath 206 is disposed between third wire 260 and fourth wire 266 of proximal coil 232. In a preferred embodiment, sheath 206 comprises a non-conductive material. Also in a preferred embodiment, sheath 206 is disposed about third wire 260 and extends longitudinally along substantially the entire length of third wire 260.

A distal end 222 of first wire 202 and a distal end 224 of second wire 204 are coupled to form a junction 240. In the embodiment of FIG. 3, junction 240 includes a tip member 242 disposed between distal end 222 of first wire 202 and a distal end 224 of second wire 204. In a preferred embodiment, tip member 242 comprises an electrically conductive material. Tip member 242 may be formed, for example, by depositing solder on the distal ends of first wire 202 and second wire 204.

In a preferred embodiment, first wire 202 comprises a first material 234 and second wire 204 comprises a second material 236 which is different than first material 234. Also in a preferred embodiment, first material 234 and second material 236 are selected so that an electromotive force is produced across junction 240. In a particularly preferred embodiment, first material 234 and second material 236 are selected so that the amplitude of the electromotive force across junction 240 varies with changes in the temperature of junction 240. Also in a particularly preferred embodiment, the amplitude of the electromotive force produced by junction 240 varies with the temperature of a tissue proximate junction 240 (i.e., the temperature of junction 240 is effected by the temperature of tissue proximate junction 240).

In a preferred embodiment, third wire 260 and fourth wire 266 each comprise an electrically conductive material. Examples of electrically conductive materials which may be suitable in some applications include stainless steel, tantalum, gold, titanium, and Nitinol. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

The term "wire", as used in describing first wire 202, second wire 204, third wire 260, and fourth wire 266 should not be mistaken as limiting these wires to elements having a circular cross section. The cross section of these wires may be any number of shapes. For example, the cross section of the wires could be rectangular, elliptical, etc. Likewise, the term "wire", as used in describing these elements should not be mistaken as being limited to metallic materials. In fact, these elements may comprise many metallic and non-metallic materials. Examples of non-metallic materials which may be suitable in some applications include conductive thermoplastic materials and thermoplastic materials filled with conductive powder.

Figure 4:
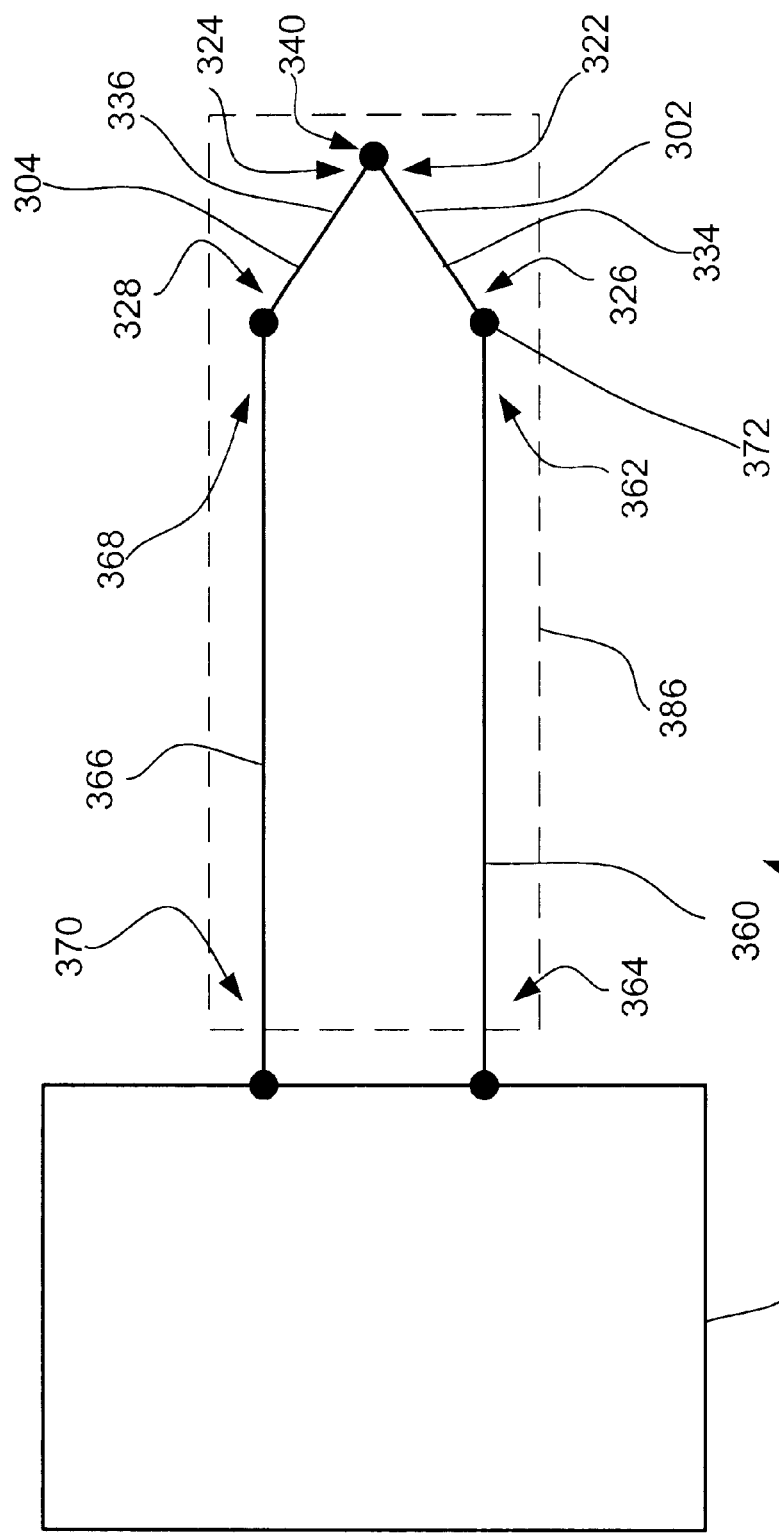
FIG. 4 is a schematic diagram of a system for detecting vulnerable plaque within a blood vessel, in accordance with an exemplary embodiment of the present invention.

FIG. 4 is a schematic diagram of a system 380 for detecting vulnerable plaque within a blood vessel, in accordance with an exemplary embodiment of the present invention. System 380 includes an elongate medical device 386. Elongate medical device 386 may be, for example, a guidewire, a catheter, etc. Elongate medical device 386 includes a first wire 302 and a second wire 304. A distal end 322 of first wire 302 is coupled to a distal end 324 of second wire 304 to form a junction 340. A proximal end 326 of first wire 302 is coupled to a distal end 362 of a third wire 360 at a first joint 372. In a similar fashion, a proximal end 328 of second wire 304 is coupled to a distal end 368 of a fourth wire 366. A proximal end 364 of third wire 360 and a proximal end 370 of fourth wire 366 are each coupled to an instrument 388.

In a preferred embodiment, first wire 302 comprises a first material 334 and second wire 304 comprises a second material 336 which is different than first material 334. In this preferred embodiment, first material 334 and second material 336 are selected so that an electromotive force is produced across junction 340. In a particularly preferred embodiment, first material 334 and second material 336 are selected so that the amplitude of the electromotive force across junction 340 varies with changes in the temperature of junction 340. As shown in FIG. 4, instrument 388 is coupled to first wire 302 and second wire 304 via third wire 360 and fourth wire 366, respectively. In a preferred embodiment, instrument 388 may be utilized to measure the amplitude of the electromotive force across junction 340. In a particularly preferred embodiment, the amplitude of the electromotive force produced by junction 340 varies with the temperature of a tissue proximate junction 340 (i.e., the temperature of junction 340 is effected by the temperature of tissue proximate junction 340).

Figure 5:
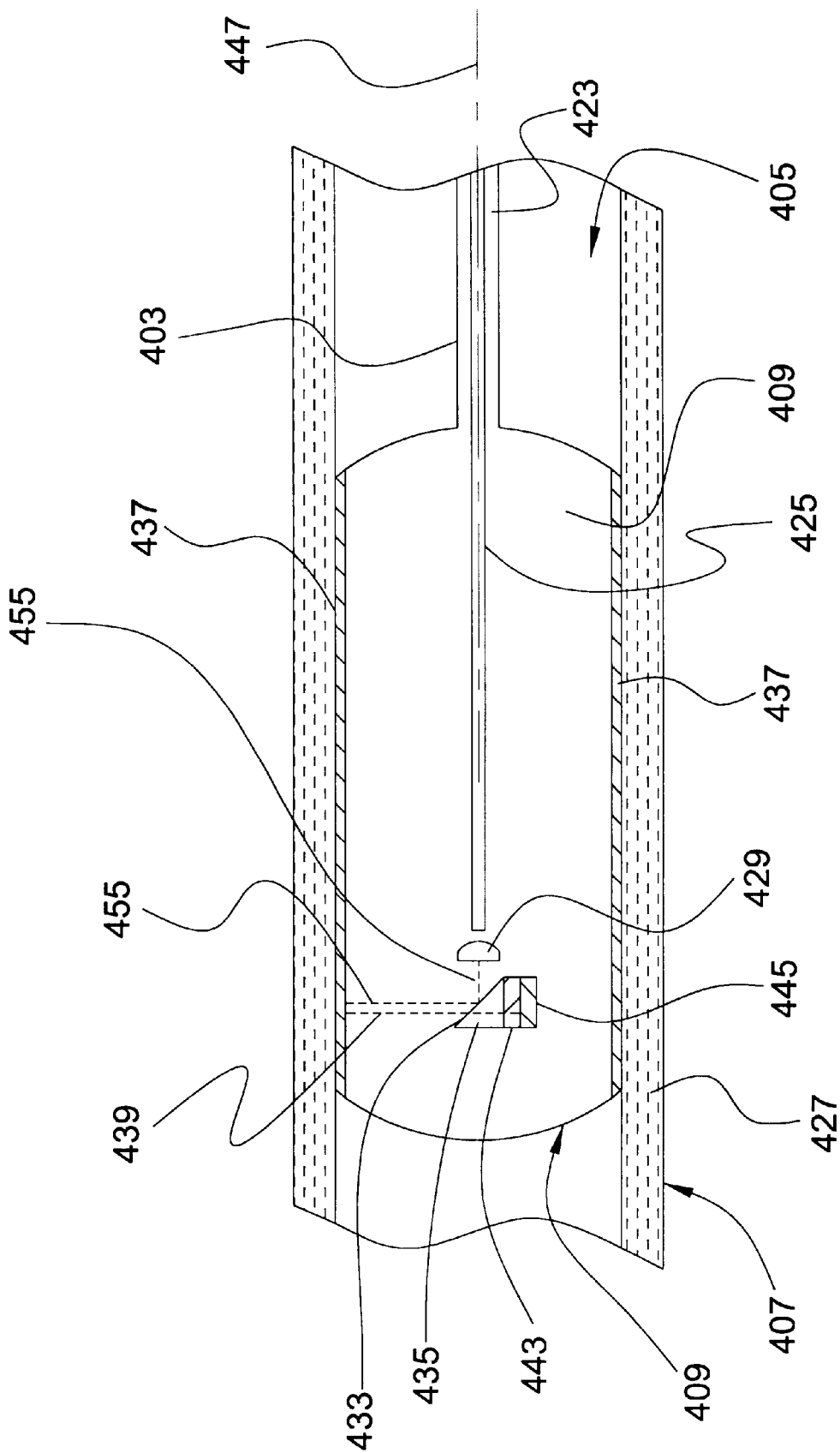
FIG. 5 is a partial cross-sectional view of a catheter in accordance with an additional exemplary embodiment of the present invention.

FIG. 5 is a partial cross sectional view of a catheter 405 in accordance with an exemplary embodiment of the present invention. Catheter 405 includes a shaft 403 defining a lumen 423, and a balloon 409 disposed about shaft 403 proximate it's distal end. An optical fiber 425 is disposed within lumen 423 of shaft 403.

In FIG. 5, catheter 405 is shown disposed within the lumen of a blood vessel 407. In FIG. 5, balloon 409 is shown in an inflated state. When balloon 409 is in the inflated state, balloon 409 preferably contacts a wall 427 of blood vessel 407 and the flow of blood through the lumen of blood vessel 407 is occluded. Balloon 409 preferably also has a deflated state in which balloon 409 and catheter 405 have a low profile and blood flow through blood vessel 407 is not precluded.

In one method in accordance with the present invention, light of a selected wavelength passes through optical fiber 425. The light is collimated by a lens 429 and is partially reflected by a partially reflecting surface 433 of a reflector 435. After being reflected, the light impinges on a layer 437 of balloon 409.

Layer 437 of balloon 409 preferably has temperature dependent optical properties. Various temperature dependent optical properties are possible without deviating from the spirit and scope of the present invention. For example, layer 437 may comprise a material which changes polarization at a defined temperature. By way of a second example, layer 437 may comprise a liquid crystal material which changes color as a function of temperature. Embodiments of the present invention have been envisioned in which layer 437 is encapsulated between an outer layer and an inner layer of balloon 409.

A portion of the light 455 impinging on layer 437 is reflected by layer 437 to produce a light signal 439. This light signal 439 passes through partially reflecting surface 433. A portion of light signal 439 also passes through a filter 443 so that it illuminates a detector 445. Detector 445 may comprise various light sensors without deviating from the spirit and scope of the present invention. Examples of light sensors which may be suitable in some applications include photodiodes, phototransistors, photovoltaic cells, and photoresistors.

Filter 443 is preferably adapted to differentially transmit light depending on the wavelength of the light. For example, if layer 437 turns red at a temperature a few degrees above 37° C., then filter 443 may be selected to transmit red light. In this exemplary embodiment, the signal produced by detector 445 will be higher when layer 437 turns red due to warming by vulnerable plaque.

During a procedure, reflector 435 may be rotated about a central axis 447. Reflector 435 may also be pulled back along central axis 447, preferably at a constant speed. The angular orientation and axial position of reflector 435 may be used to define the portion of blood vessel 407 which is being illuminated at any given point during the procedure. Thus, the position of any vulnerable plaque may be identified by observing variations in the signal from detector 445 and correlating those changes with the angular orientation and axial position of reflector 435.

Embodiments of catheter 405 have been envisioned which include an ultrasonic transducer disposed within balloon 409. A signal produced by this ultrasonic transducer may be utilized to produce an ultrasound image. The signals collected from detector 445 may be combined with the signal collected from the ultrasonic transducer so that each point in the ultrasound image is displayed with a temperature dependant color. The areas which are likely to include vulnerable plaque may be marked in the ultrasound image using a selected color.

Figure 6:
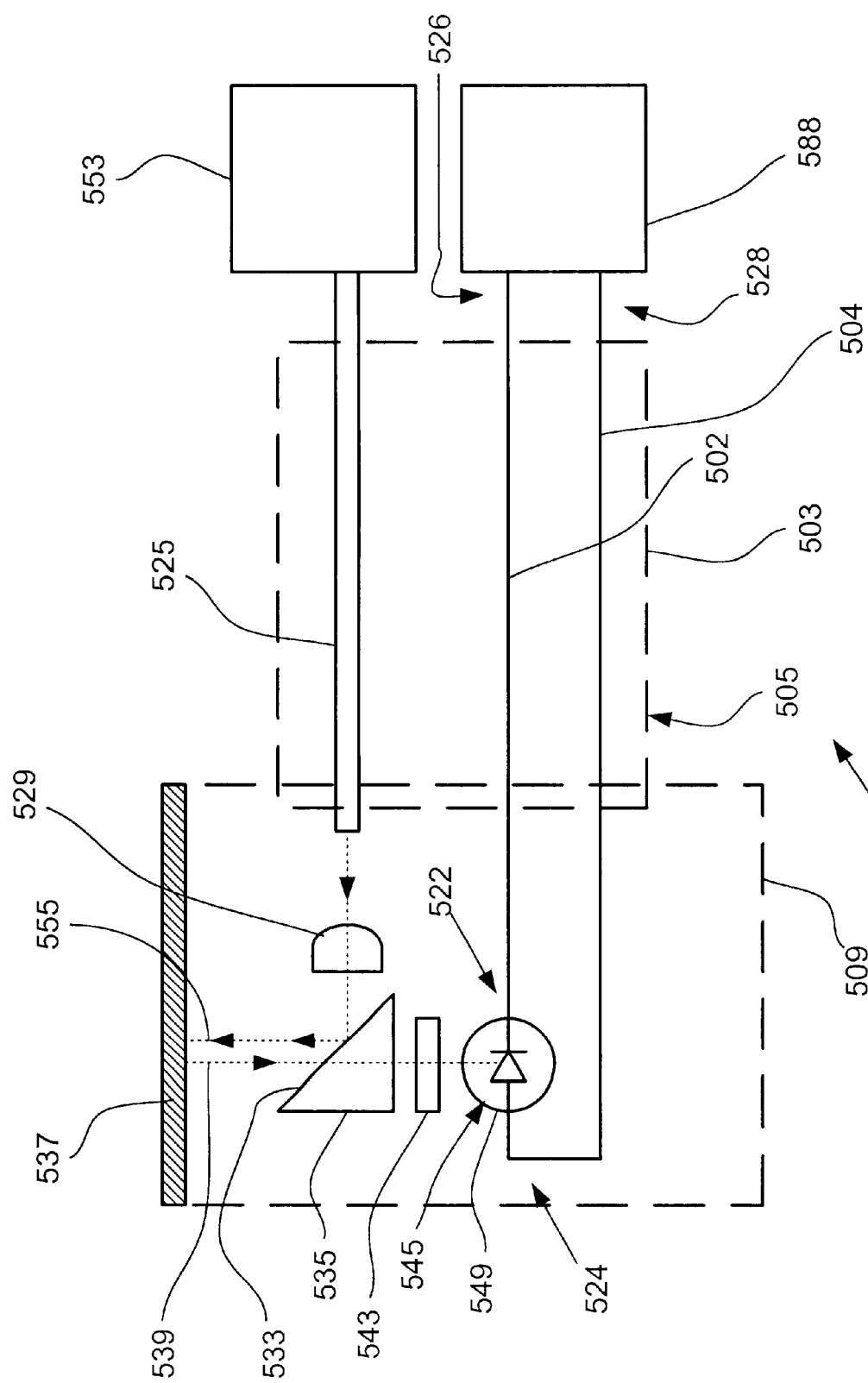
FIG. 6 is a diagrammatic representation of a system for detecting vulnerable plaque within a blood vessel, in accordance with an exemplary embodiment of the present invention.

FIG. 6 is a diagrammatic representation of a system 580 for detecting vulnerable plaque within a blood vessel, in accordance with an exemplary embodiment of the present invention. System 580 includes a catheter 505 comprising a shaft 503 and a balloon 509. Catheter 505 includes a first wire 502 having a distal end 522 coupled to a detector 545 and a proximal end 526 coupled to an instrument 588. Catheter 505 also includes a second wire 504 having a distal end 524 coupled to detector 545 and a proximal end 528 coupled to instrument 588. In a preferred embodiment, detector 545 produces a voltage which varies with the temperature of tissue located proximate balloon 509 of catheter 505. In the embodiment of FIG. 6, detector 545 comprises a photodiode 549. Detector 545 may comprise other detectors without deviating from the spirit and scope of the present invention. Examples of detectors which may be suitable in some applications include phototransistors and photovoltaic cells.

Catheter 505 of FIG. 6 also includes an optical fiber 525. A distal end of optical fiber 525 is coupled to a light source 553. Light from light source 553 passes through optical fiber 525, and is collimated by a lens 529. This light is partially reflected by a partially reflecting surface 533 of a reflector 535 so that it illuminates a portion of a layer 537 of balloon 509. Layer 537 of balloon 509 preferably has temperature dependent optical properties which may effect, for example, the wavelength and/or intensity of the light which is reflected by layer 537. The portion of light 555 which is reflected by layer 537 forms a light signal 539. This light signal 539 passes through partially reflecting surface 533. A portion of light signal 539 also passes through a filter 543 so that it illuminates detector 545.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A system for detecting vulnerable plaque within a blood vessel, comprising:

a first wire having a distal end and a proximal end;

a second wire having a distal end and a proximal end;

wherein the second wire includes a coiled portion having a plurality of turns coiled about at least a portion of the first wire;

a voltage source coupled to the distal end of the first wire and the distal end of the second wire, the voltage source producing a voltage that is dependent on the temperature of tissue proximate to the voltage source; and a means for measuring voltage coupled to the proximal end of the first wire and the proximal end of the second wire.

2. The system of claim 1, wherein an amplitude of an electromotive force produced by the voltage source varies with a temperature of the voltage source.

3. An elongate medical device, comprising:

a first wire comprising a first material;

a second wire comprising a second material different from the first material;

wherein the second wire includes a coiled portion having a plurality of turns coiled about at least a portion of the first wire;

a distal portion of the second wire being coupled to a distal portion of the first wire to form a junction; and wherein the junction produces an electromotive force whose magnitude is dependent on the temperature of tissue proximate to the junction.

4. The elongate medical device of claim 3, wherein an amplitude of the electromotive force varies with a temperature of the junction.

5. The elongate medical device of claim 3, further including an insulator disposed between the first wire and the second wire.

6. The elongate medical device of claim 3, further including a sleeve disposed about the first wire.

* * * * *

UNITED STATES PATENT AND TRADEMARK OFFICE
CERTIFICATE OF CORRECTION

PATENT NO. : 6,694,181 B2
DATED : February 17, 2004
INVENTOR(S) : Jaydeep Y. Kokate, Eric M. DoBrava and Michael J. Urick It is certified that error appears in the above-identified patent and that said Letters Patent is hereby corrected as shown below:

<u>Title page,</u>
Item [75], Inventors, "Jaydeep Y. Kokate", please delete "US" and insert -- India -- therefor; and "Michael J. Urick", please delete "CA" and insert -- US -- therefor.

Signed and Sealed this

Ninth Day of August, 2005

JON W. DUDAS
*Director of the United States Patent and Trademark Office*